(12) United States Patent
Mazor et al.

(10) Patent No.: US 7,960,456 B2
(45) Date of Patent: Jun. 14, 2011

(54) HALOGENATED PHOSPHONATES, PROCESSES FOR THEIR PREPARATION AND THEIR USE AS FLAME RETARDANTS

(75) Inventors: Royi Mazor, Beit-Kama (IL); Asher Shoshan, Beer-Sheva (IL); Michael Peled, Beer-Sheva (IL)

(73) Assignee: Bromine Compounds Ltd., Beer-Sheva (IL)

( * ) Notice: Subject to any disclaimer, the term of this patent is extended or adjusted under 35 U.S.C. 154(b) by 0 days.

(21) Appl. No.: 12/787,863

(22) Filed: May 26, 2010

(65) Prior Publication Data

US 2010/0305252 A1    Dec. 2, 2010

Related U.S. Application Data

(60) Provisional application No. 61/181,304, filed on May 27, 2009.

(51) Int. Cl.
*C08K 5/5337* (2006.01)
*C08K 5/5357* (2006.01)

(52) U.S. Cl. .......................... 524/132; 524/131; 558/214

(58) Field of Classification Search .................. 524/131, 524/132; 558/214
See application file for complete search history.

(56) References Cited

U.S. PATENT DOCUMENTS

| 3,325,569 | A | 6/1967 | D'Alelio |
| 4,036,809 | A | 7/1977 | Keblys |

FOREIGN PATENT DOCUMENTS

| EP | 0524023 | 1/1993 |
| EP | 1751223 | 2/2007 |
| GB | 1338682 | 11/1973 |
| GB | 2228939 | 9/1990 |
| WO | 2006/124760 | 11/2006 |
| WO | 2010/046896 | 4/2010 |
| WO | 2010/046898 | 4/2010 |

OTHER PUBLICATIONS

Liaw et al, "Synthesis of Some Dialkyl Bromo-Substituted Benzyl Phosphonates,"Journal of the Chinese Chemical Society 31(3), pp. 11-14 (1984).

*Primary Examiner* — Peter Szekely
(74) *Attorney, Agent, or Firm* — Dilworth & Barrese, LLP.

(57) ABSTRACT

A compound having the formula:

(I)

$$\text{Hal}_n\text{-C}_6\text{H}_4\text{-CH}_2\text{-P(=O)(OR)-O-CH}_2\text{-C}_6\text{H}_4\text{-Hal}_m$$

Wherein Hal independently indicates a halogen atom;

R is selected from the group consisting of a straight or branched, optionally substituted C1-C5 alkyl and halogenated benzyl; and m and n are, independently, integers in the range between 3 and 5, inclusive.

14 Claims, No Drawings

HALOGENATED PHOSPHONATES, PROCESSES FOR THEIR PREPARATION AND THEIR USE AS FLAME RETARDANTS

The invention provides a class of compounds having the formula:

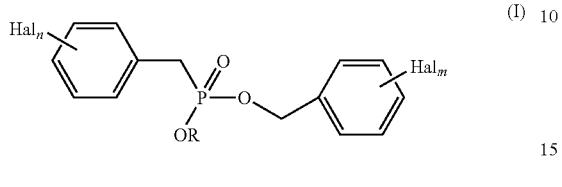

Wherein Hal independently indicates a halogen atom (e.g. chlorine or bromine, preferably bromine);

R is selected from the group consisting of a straight or branched, optionally substituted C1-C5 alkyl and halogenated benzyl; and m and n are, independently, integers in the range between 3 and 5, inclusive. Preferably, m and n are independently 4 or 5. More preferably, the aromatic rings are perhalogenated.

The compounds of Formula I are useful as flame retarding agents in flammable materials, e.g. in thermoplastics.

In a preferred sub-class of the compounds of Formula I, R is a straight or branched, optionally substituted C1-C5 alkyl group. Compounds belonging to this sub-class are hereinafter sometimes identified as "compounds (Ia)". Compounds (Ia) contain two aromatic rings, which are preferably perhalogenated (namely, n and m each equals 5). More preferably, all the ten halogen atoms attached to the aromatic rings are bromine atoms. An especially preferred compound belonging to this sub-class is ethyl perbromobenzyl perbromobenzylphosphonate, which is represented by the formula depicted below:

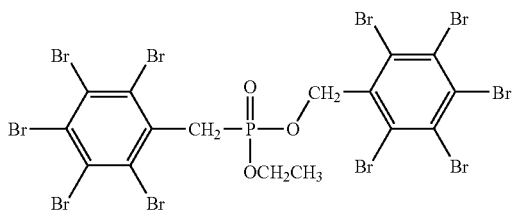

In another preferred sub-class of the compounds of Formula I, R is halogenated benzyl. Compounds belonging to this sub-class are hereinafter sometimes identified as "compounds (Ib)". Compounds (Ib) contain three aromatic rings, each of which is preferably perhalogenated. More preferably, the halogen atoms attached to the three aromatic rings are all bromine atoms. A particularly preferred compound belonging to this sub-class has the formula depicted below (chemically named bis(perbromobenzyl)perbromobenzylphosphonate):

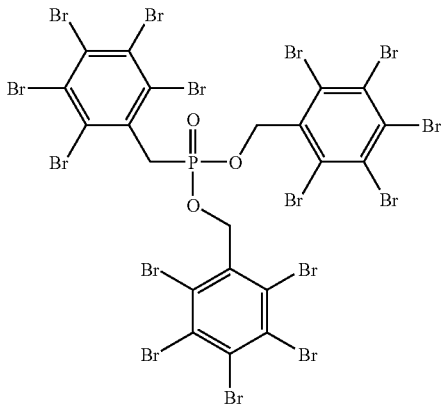

A useful synthetic route for preparing the compounds of Formula I is represented by the following reaction scheme:

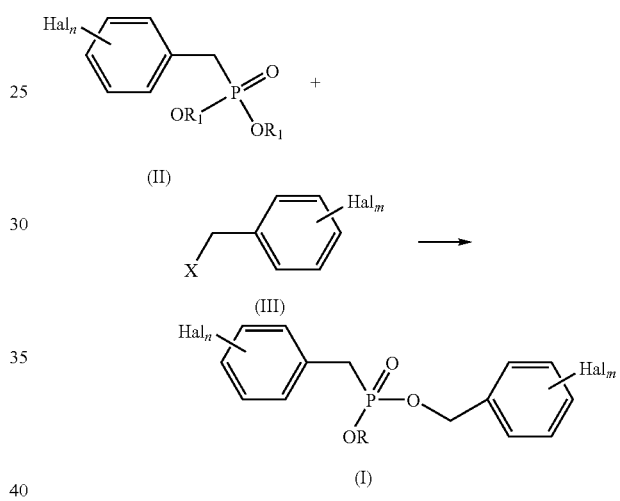

Wherein Hal, n, in and R have the meanings indicated above, $R_1$ is a straight or branched, optionally substituted C1-C5 alkyl group and X is a leaving group, specifically halogen (e.g., chlorine or bromine).

The reactants of Formula II and their preparation are known in the art and are described in GB 2,228,939; Liaw et al. [Journal of the Chinese Chemical Society, 31(3) p. 11-14 (1984)]; and WO 2006/124760 (Example 2t). In general, the synthetic route for preparing the compounds of Formula II involves a reaction between halogenated benzyl halide and trialkyl phosphite [$P(OR_1)_3$, wherein $R_1$ is an alkyl group] in a solvent, followed by the precipitation and isolation of the compound of Formula II. The compounds of Formula II are also commercially available (for example, FR-564 from ICL-IP).

The halogenated benzyl halide reactants of Formula III, wherein X is chlorine or bromine, are also well known in the art. Their preparation is based on the halogenation of toluene in the presence of a Lewis acid catalyst, whereby the substitution on the aromatic ring is achieved. The subsequent halogenation of the methyl group in order to introduce the benzyl halide functionality is carried out in an organic solvent in the presence of chlorine or bromine and a radical initiator under conditions known in the art. The compounds of Formula III are also commercially available (for example, FR-706 from ICL-IP).

The reaction depicted above, between the starting materials of Formulas (II) and (III), is carried out in a liquid medium. It has been found that the compound of Formula (II) may be conveniently used both as a reactant and as a liquid component of the reaction mixture, in view of its capacity to dissolve the reactant of Formula (III) and to allow, upon completion of the reaction, a relatively easy separation of the final product of Formula (I) from the reaction mixture. Since the starting material of Formula (II) is in a solid state at room temperature, the reaction is carried out under heating, at a temperature above the melting point of said starting material, whereby said starting material of Formula (II) is maintained in a liquid, molten form during the reaction. The table below reports the melting points for some useful starting materials of Formula (II) (see Liaw et al., supra):

TABLE I

| Compound of Formula II | HAL | n | R1 | $T_{melting}$ |
|---|---|---|---|---|
| 1 | Br | 3 | —$CH_3$ | ~93-95° C. |
| 2 | Br | 5 | —$CH_3$ | ~133-136° C. |
| 3 | Br | 5 | —$CH_2CH_3$ | ~123-124° C. |
| 4 | Br | 5 | —$CH(CH_3)_2$ | ~113-115° C. |
| 5 | Br | 5 | —$(CH_2)_3CH_3$ | ~76-78° C. |

Accordingly, the present invention also relates to a process, which comprises providing the compound of Formula (II) in a liquid form, mixing said liquid with a compound of formula (III) at a temperature above the melting point of said compound of Formula (II) to form the product of Formula (I), and separating said product from the reaction mixture.

Thus, according to the present invention, the reaction mixture does not require the presence of a non-indigenous diluent or solvent (by the term "non-indigenous diluent or solvent" is meant a liquid substance which is not involved in the reaction). In view of its twofold function, as a diluent/solvent and a reactant, the compound of Formula (II) is used in a molar excess relative to the compound of Formula (III). In general, from about 1.1 to 5 moles of the compound of Formula (II) are employed per mole of the halogenated benzyl halide of Formula (III). The reaction is carried at a temperature which is preferably 25 to 50 degrees above the melting point of the reactant of Formula (II) for about 1 to 48 hours, and is accompanied by the evolution of alkyl halide ($R_1X$) by-product, which is preferably removed from the reaction mixture by distillation.

In conducting the process, the compound of Formula (II) is fed to a reaction vessel and maintained therein in a liquid form, in which the halogenated benzyl halide of Formula (III) is dissolved. The reaction is preferably carried out under inert atmosphere to prevent side reactions. Such an atmosphere can be provided by inert gases such as nitrogen, argon and the like. The reaction mixture is stirred and the product of Formula (I) generally precipitates from the liquid phase during the course of the reaction, such that the reaction mixture turns into a slurry which contains a liquid phase, consisting of the reactant of formula (II), and a solid phase, consisting of the product of Formula (I). The progress of the reaction may be monitored by HPLC analysis, wherein the disappearance of the halogenated benzyl halide reactant of Formula (III) signifies the completion of the reaction.

In the synthetic route described above, the starting material of Formula II is used in a liquid (molten) form, providing a stirable liquid reaction medium in which the reaction with the halogenated benzyl halide of Formula (III) may proceed smoothly to give the product of formula I. The starting material of Formula II is available in a solid form, either commercially or by using the synthetic procedures outlined in the references mentioned above (GB 2,228,939; Liaw et al.; WO 2006/124760, supra). The solid starting material of Formula II can be melted, to obtain a molten material operative according the process of the invention. However, it is also possible to obtain the reactant of Formula II as a high purity melt, using the methods described in co-owned U.S. patent application Nos. 60/107,690 and 61/146,329. The molten material thus obtained may be directly employed in the process of the present invention. The in-situ preparation of the compound of formula II, and its capacity to serve as a reactant and a liquid component of the reaction mass, provide the basis for making the product of formula (I) by means of one-pot synthesis, as described in detail below.

In order to obtain the starting material of Formula II in a molten form, trialkyl phosphite is reacted with halogenated benzyl halide of Formula (III) in a reaction vessel which is free of non-indigenous solvent/diluent. The reaction vessel is heated to a sufficiently high temperature, maintaining the progressively formed compound of Formula II in a liquid state, and providing a stirable reaction mixture. The alkyl halide by-product is removed from the reaction mixture, either concurrently with or subsequent to the reaction, such that a reaction mass is finally obtained, consisting essentially of the compound of Formula (II) in a molten state. The resulting molten material is of high purity, and may be employed directly, without being subjected to purification procedures, as a reactant in the process of the invention. A complete preparative procedure, illustrating the synthesis of diethyl pentabromobenzylphosphonate (abbreviated DEPBBP and also identified herein as FR-564) as high purity liquid substance useful as a starting material according to the present invention is given in the Examples section under the title "Preparation 1".

Thus, in a preferred embodiment of the process set forth above, the compound of formula (II) is provided in-situ in a molten form, by means of reacting halogenated benzyl halide of formula (III) with trialkyl phosphite of the formula $(R_1O)_3P$, wherein said compound of formula (II) functions as an indigenous reaction liquid medium.

As noted above, it is also possible to prepare the product of formula (I) by means of one-pot synthesis, by reacting trialkyl phosphite and halogenated benzyl halide (III), to produce the compound of Formula (II) in a liquid form, and allowing said compound (II) to proceed and react with the halogenated benzyl halide (III), to give the product of formula (I). The molar ratio between the halogenated benzyl halide of Formula (III) and the trialkyl phosphite starting materials is adjusted in order to satisfy two conflicting demands. There must be sufficient amount of the halogenated benzyl halide (III) to be consumed by the intermediate (II), in order to give appreciable quantities of the desired product (I). Yet, since the intermediate (II) must serve as a liquid component for providing a stirable reaction mass throughout the synthesis, it cannot be allowed to transform completely into the product (I). In general, a workable molar ratio of halogenated benzyl halide (III) trialkyl phosphite is in the range between 3:1 and 1:1 and more preferably between 3:2.5 and 3:1.5.

The one-pot process for preparing the compound of formula (I), using trialkyl phosphite and halogenated benzyl halide of Formula (III) as the starting materials, as outlined above, is illustrated by the following reaction scheme:

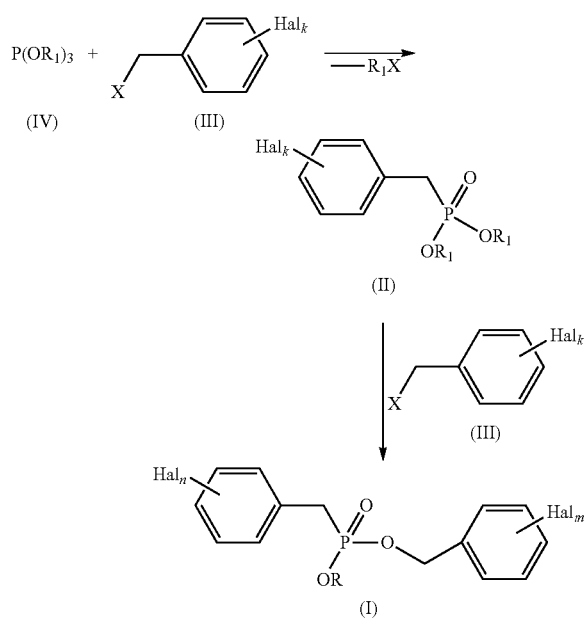

Wherein $R_1$, Hal, m, n and R have the meanings set forth above and k is either m or n.

The present invention thus provides a one-pot process for preparing the product of formula I, which comprises reacting halogenated benzyl halide of formula (III) with trialkyl phosphite of the formula $(R_{10})_3P$ under heating, to obtain a compound of formula (II) in a liquid form, maintaining the reaction mixture at a temperature above the melting point of said compound (II) for a sufficient time to form the product of formula (I), and separating said product from the reaction mixture.

One possible way of carrying out the one-pot reaction according to the present invention comprises adding the halogenated benzyl halide (III) and the liquid trialkyl phosphite (IV) to a reaction vessel, wherein the former is applied in excess relative to the latter, heating the reaction mixture (free of a non-indigenous diluent or solvent) under stirring to gradually form a solution, maintaining the reaction mass in a liquid state and distilling the haloalkane by-product. The reaction is preferably carried out under inert atmosphere to prevent side reactions, as described above. It should be noted that the reaction is exothermic. The temperature of the reaction mass during at least a substantial portion of the reaction is above the melting point of the compound of formula II, and preferably below the boiling point of the trialkyl phosphite of the formula $(R_1)_3P$. More specifically, the temperature of the reaction mixture may be in the range between 80 and 180° C., and even more specifically, between 100 and 150° C. (during the formation of the compound of formula (II)). A sharp drop of the temperature of the reaction mixture indicates that the formation of the compound of formula II has been essentially completed. The temperature is kept about 20-40 degrees above the melting point of the compound (II) by heating the reaction mixture. Preferably, the reaction vessel is heated to about 150-180° C., and is kept at the selected temperature for an additional period of time, e.g., about 1 to 24 hours, during which the excess halogenated benzyl halide (III) starting material reacts with the compound of formula (II) to give the product of formula (I), which generally spontaneously precipitates from the liquid reaction mixture.

In view of the release of heat associated with the formation of the compound of formula (II), it may be sometimes desirable to carry out the reaction under more controllable conditions. In this regard, it has been found useful to provide in the reaction vessel an amount of the compound of formula (II) in a molten state, prior to the addition of the starting materials. The ratio between the initially charged molten compound of formula (II) to the halogenated benzyl halide starting material of formula (III) may be in the range between 1:1 and 1:10, such that the initially charged molten compound (II) preferably occupies about 15-25% of the reactor's volume. According to this variant of the invention, the temperature of the reaction vessel (which is free of a non-indigenous diluent or solvent), is kept above the melting point ($T_{melting}$) of the compound (II) already from the beginning, thus holding the initially charged compound (II) in a molten state, while the starting material of formula (III) is being charged to the reaction vessel to form a stirable slurry with the molten material (it is possible to introduce additional amounts of the halogenated benzyl halide (III) at later stages of the reaction). Then, the other reactant—the trialkyl phosphite—is gradually fed to the reaction vessel. The addition of the trialkyl phosphite is preferably carried out over a period of time, wherein the rate of the addition is adjusted in order to control the exothermic behavior of the reaction and the evolution of the alkyl halide by-product. More specifically, the gradual addition of the trialkyl phosphite into the reaction vessel may be accomplished either continuously, over a period of time of not less than 30 minutes at an approximately constant rate or in a portion-wise manner, such that approximately equal quantities of the trialkyl phosphite are sequentially charged into the reaction mixture over a period of time, at intervals of about 5 to 10 minutes, for example. The rate of addition generally depends on the reaction scale and the controllability of the temperature, namely, the removal of the heat generated by the reaction. On industrial scale, the gradual addition of the trialkyl phosphite may require a number of hours and the rate of addition may be adjusted according to the considerations noted above. Preferably, the trialkyl phosphite is fed to the reaction vessel through a dipping funnel, either below or above the level of the liquid contained in the reaction vessel. It has been observed that following the addition of approximately 25% of the contemplated stoichiometric amount of trialkyl phosphite, the reaction mixture slurry turns into a solution. The addition of the trialkyl phosphite starting material then continues at a rate such that the temperature of the reaction mass does not exceed 130-150° C. Under the feeding method set forth above, the distillation of the alkyl halide by-product is gently accomplished.

Having completed the gradual addition of the trialkyl phosphite starting material according to this feeding method of the invention, the preparation of the compound of formula (II) is allowed to reach completion, (signaled by a temperature drop). The reaction mass comprises the compound (II) in a molten state, and the halogenated benzyl halide (III). The reaction mass is then heated and brought to higher temperature (about 150-180° C.) and is kept in said temperature for 1-24 hours, to allow the compound of formula (II) to react with the halogenated benzyl halide (III), and to give the product of formula (I). HPLC analysis may be used to determine the complete consumption of the halogenated benzyl halide (III) and hence, the end of the reaction.

Upon completion of the synthesis stage (which may be run by any one of the reaction schemes outlined above), the solid product of Formula (I) is separated from the liquid phase of the reaction mass, which consists of the starting material of Formula (II) in a molten state, by means of any suitable method. It has been observed that the crude product is generally obtained as a mixture comprising two compounds of formula I: compound (Ia), in which R is a straight or branched, optionally substituted C1-C5 alkyl group and a compound (Ib), in which R is halogenated benzyl group. An illustrative mixture of compounds (Ia) and (Ib) obtainable by the process of the invention consists of the following pair of compounds:

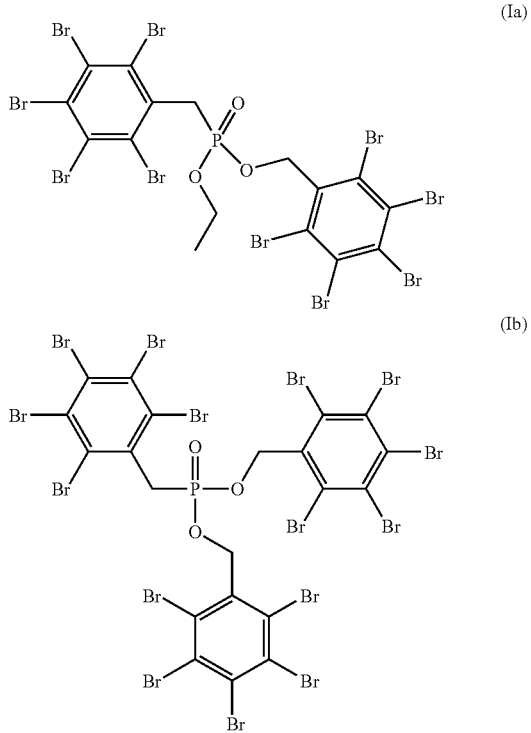

The ratio between the two components of the product mixture may vary in a wide range, between 1:1 and 1:100. The ratio between the two components (Ia:Ib) generally depends on amount of FR-706 in the reaction mixture.

If desired, the crude, solid products mixture may be treated in order to obtain each compound of formula (I) in a substantially pure form, as described in more detail below. However, from utility perspective, the separation of the mixture into its components is not mandatory, and the mixture of products of formula (I) may be used as such for retarding the flammability of flammable materials.

The process of the present invention may therefore comprise the step of obtaining a mixture of compounds of formula (I), and enriching the mixture with respect to one component (either Ia or Ib), and optionally also separating, essentially completely, the mixture into its components. A convenient, method for separating the crude, solid product mixture from the liquid phase of the reaction mass, and for isolating each of the components of the mixture in a substantially pure form, may be carried out as follows. Upon completion of the chemical reaction, a first organic solvent is added to the reaction slurry, which first organic solvent is miscible with the liquid phase of the reaction mass (namely, with the compound of Formula (II)), yet said first organic solvent is capable of dissolving only one of the components of the solid product mixture, or none of them, such that following the addition of said first organic solvent into the reaction mass, the product is at least partially maintained in a solid form. The solid phase is then separated from the liquid phase by means of hot filtration, to obtain a first crop of the solid product and a first filtrate.

In the event that the first crop of the solid product consists of a mixture of compounds of formula (I)—and in practice, this may often be the case—then the first product crop may be subsequently treated in order to obtain each of its two components in a substantially pure form. To this end, the first crop of the solid product may be treated in a second organic solvent, in which the two components of the product mixture exhibit distinct solubility profiles. It should be noted that the first and second organic solvents used may be the same or different. The component of the mixture which is insoluble in said second organic solvent is then separated from the liquid phase (e.g., by filtration or centrifugation), whereby a second filtrate is formed in which the other component of the mixture is present as a solute. This component may be then recovered from the second filtrate by means of known techniques (such as concentration of the solution, e.g., evaporation of the solvent and extraction).

It should be noted that the first filtrate obtained following the separation of the first crop of the product of formula (I) from the reaction mass should preferably be tested for the presence of said product, which may be present in the first filtrate as a solute, and additional crops of the product may be recovered from said first filtrate, if desired.

Organic solvents which are suitable for accomplishing the separation procedures set forth above include halogenated aromatic solvents, such as chlorobenzene. The compounds Ia and Ib are separable from one another in hot chlorobenzene, since they are soluble and insoluble, respectively, in hot chlorobenzene. Following the addition of an excess of chlorobenzene (relative to compound II) into the reaction slurry which consists of the compound of formula (II) in a liquid form and the solid product of formula (I), the solid product is separated from the resultant mixture by means of hot filtration. The solid collected, enriched with respect to the Ib compound, can be further purified by means of successive treatments in hot chlorobenzene (at a temperature of about 80 degree and higher).

The compounds of Formula I have been found useful as flame retardant agents in a flammable material. Accordingly, another aspect of the present invention is a flame retarded formulation which comprises a flammable material (e.g., a polymer) and one or more compounds of formula (I).

Specific polymers which can be formulated together with the compound of formula (I) include olefin polymers (either homopolymers or copolymers) and also styrene-containing polymers. The latter term, as used herein, includes polystyrene (e.g. high impact polystyrene) and also styrene copolymers (including terpolymers), which contain (optionally substituted) styrenic structural unit, however combined with one or more other structural units. Preferred are terpolymers that include the structural units corresponding to (optionally substituted) styrene, acrylonitrile and butadiene (abbreviated ABS).

Preferably, the formulation comprises not less than 50% by weight of the polymer, and more preferably not less than 70% (e.g. between 70-80%), together with a flame-retarding effective amount of the compound of formula (I). The precise amount of the compound of formula (I) in the formulation is adjusted in order to achieve the desired level of flame retardancy. The flammability characteristics of plastic materials are quantifiable according to the method specified by Underwriter Laboratories standard UL 94. The UL 94 ratings are V-0, V-1, and V-2. A material assigned with the V-0 rating is considered to be the less flammable. For certain applications the lower V-2 rating is acceptable, whereas for other applications the more strict V-1 and V-0 ratings are needed. The formulation according to the invention generally contains between 10 and 30% weight percent, preferably between 12 and 18% of the compound of formula (I), assuming that it is the only flame retardant agent used. As illustrated hereinbelow, V-0 rated ABS formulation is attainable by incorporating therein the compound of formula (I) in an amount of less than 18% by weight.

Conventional additives may also be included in the polymeric formulation. For example, an inorganic compound (typically a metal oxide) capable of cooperating with the compound of formula (I) for retarding the flammability of the polymeric formulation is preferably also present in formulation. A preferred example of a suitable inorganic compound, which is generally considered as an "inorganic synergist", is antimony trioxide. Other illustrative additives include antioxidants, heat stabilizers, UV stabilizers and pigments.

The formulations are prepared by methods known in the art. The various ingredients of the formulation are blended together, according to their respective amounts. The ingredients may be first dry blended using suitable mixing machines, such as Henschel mixer. The resulting mixture may then be processed and compounded to form homogeneous pellets, for example, by using a twin extruder. The pellets obtained are dried, and are suitable for feed to an article shaping process such as injection molding. Other blending and shaping techniques can also be applied.

EXAMPLES

Example 1

Preparation of ethyl perbromobenzyl perbromobenzylphosphonate and bis(perbromobenzyl) perbromobenzylphosphonate Into a 100 ml round bottomed flask equipped with mechanical stirrer, nitrogen inlet, and an outlet pipe into a cooled trap (under ice), was placed diethyl pentabromobenzylphosphonate (FR-564; 20 gr., 0.032 mol). The temperature was raised to 140° C. to melt the starting material FR-564. Pentabromobenzyl bromide (PBB-Br; FR-706; 9.15 gr., 0.016 mol) was added to the melt. A solution was obtained, and the temperature was further raised to 160° C. and the reaction vessel was kept at said temperature for 20 hours. A white solid precipitated during the reaction, and the reaction mass turned into a slurry. When only traces of FR-706 were detected by HPLC analysis, the reaction mixture was cooled to 140° C. and 20 ml of chlorobenzene were added slowly. The reaction mixture was cooled to 100° C. and was filtered at this temperature (hot filtration). The white cake was washed on the filter paper with 30 ml of hot chlorobenzene followed by 50 ml of hot ethylacetate (70° C.). The product was dried at 80° C. in a vacuum oven. The product collected was in the form of a white powder (7.6 g). HPLC analysis of the filtrate indicates the presence of the starting material FR-564 and the product mixture (59 area % and 34 area %, respectively).

The solid product was treated in hot chlorobenzene. A portion of the solid dissolved. Following hot filtration, a first solid was collected. The chlorobenzene was then removed from the filtrate by evaporation and a second solid was recovered. The first and second solids were characterized as follows, respectively:
bis(perbromobenzyl)perbromobenzylphosphonate
Melting point: 310-312° C.
Elemental analysis calculated for $C_{21}H_6Br_{15}O_3P$: % Br 78.04, % P 2.02. found: % Br 78.9, % P 2.0.
Ethyl perbromobenzyl perbromobenzylphosphonate
Melting point: 208° C.
Elemental analysis calculated for $C_{16}H_9Br_{10}O_3P$: % Br 74, % P 2.9. found: % Br 74.8, % P 2.8.

Example 2

One-Pot Preparation of ethyl perbromobenzyl perbromobenzylphosphonate and bis(perbromobenzyl) perbromobenzylphosphonate Into a 1 l round bottomed flask equipped with mechanical stirrer, nitrogen inlet, and an outlet pipe into a cooled trap (under ice), were placed triethylphosphite (105 gr. 0.63 mol) and pentabromobenzyl bromide (PBB-Br, FR-706, 544 g, 0.95 mol). The mixture was gradually heated. The temperature was raised from 25° C. up to 103° C. over 40 min. Ethylbromide started to evolve at 110° C. The temperature of the heating oil was kept at 100° C. An exothermic behavior is observed. During the exothermic period, most of the FR-706 dissolved in the hot triethylphosphite and the solution attains a yellow color. The temperature rose spontaneously in the reaction vessel to 123° C. The temperature then dropped to 105° C. At this point the temperature of the heating plate was raised gradually to 160-165° C. The temperature was kept at 160° C. for 22 hours. A white solid precipitated during the reaction, and the reaction mixture turned into a slurry. When only traces of FR-706 were detected by HPLC analysis, the reaction mixture was cooled to 140° C. and 250 ml of chlorobenzene were added slowly. The reaction mixture was cooled to 100° C. and was filtered at this temperature (hot filtration). The white cake was washed on the filter paper with another 100 ml of hot chlorobenzene followed by 200 ml of hot ethylacetate (70"C). The product was dried at 80° C. in a vacuum oven. The product (210 g), which is in the form of a white powder, consists of mixture of bis(perbromobenzyl) perbromobenzylphosphonate and ethyl perbromobenzyl perbromobenzylphosphonate in a weight ratio of 3:1, respectively:
Bis(perbromobenzyl) perbromobenzylphosphonate (157.5 g, 0.1 mol)
ethyl perbromobenzyl perbromobenzylphosphonate (52.5 g, 0.05 mol)

HPLC analysis of the chlorobenzene filtrate indicates, in addition to the presence of diethyl pentabromobenzylphosphonate, also the presence of the ethyl perbromobenzyl perbromobenzylphosphonate.

Example 3

V-0 Rated ABS Formulation

The materials used for preparing the ABS polymeric formulation are listed in the table below:

TABLE II

| Material | source | function |
|---|---|---|
| Acrylonitrile butadiene styrene terpolymer, general grade | ABS Magnum 3404 ex Dow | plastic matrix |
| ethyl perbromobenzyl perbromobenzylphosphonate | See Example 1 | Flame retardant (FR) |

TABLE II-continued

| Material | source | function |
|---|---|---|
| Antimony trioxide master batch with a carrier compatible with styrene (containing 80% (w/w) Sb2O3) | A0112 ex Kafrit | FR-synergist |
| Irganox B-225 ex Ciba | Blend of Irganox 1010 and Irgafos168 | Heat stabilizer/ antioxidant |

The ingredients were compounded in a Brabender plasticorder mixing cell for 4 minutes at 210° C.; no discoloration was observed during the processing. This was followed by press molding in a press type polystat ex. Schuabenthan for 3 min at 150° C., into 3.2 mm & 1.6 mm thick plates.

The material was left in the mold for 2 more minutes at 150° C. and the press was cooled to room temperature. Standard test specimens for UL-94 at 3.2 mm & 1.6 mm were prepared. The specimens were conditioned for 48 hours at 23° C. and were then subjected to the flammability tests.

The composition of the formulation (in terms of weight percent of the ingredients) and its flammability characteristics are reported in table III and IV, respectively. The bromine content of the formulation was 12% weight percent.

TABLE III

| Ingredients | Weight percent |
|---|---|
| ABS | 78.6% |
| ethyl perbromobenzyl perbromobenzylphosphonate | 16.2% |
| AO 112 (antimony trioxide) | 5 (4)% |
| Irganox B-225 | 0.2% |

The results of the flammability tests are reported in the Table IV:

TABLE IV

| Flammability 1.6 mm | |
|---|---|
| Max flaming time (seconds) | 1 |
| Total flaming time (seconds) | 5 |
| Specimens dripped | 0 |
| Specimens ignited cotton | 0 |
| Rating | V-0 |
| Flammability 3.2 mm | |
| Max flaming time (seconds) | 1 |
| Total flaming time (seconds) | 1 |
| Specimens dripped | 0 |
| Specimens ignited cotton | 0 |
| Rating | V-0 |

Preparation 1

Preparation of diethyl pentabromobenzylphosphonate as High Purity Melt (a Starting Material Useful in the Process of the Invention)

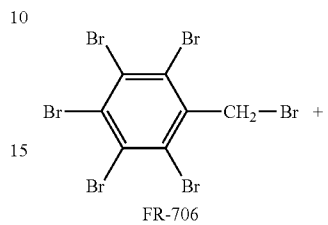
FR-706

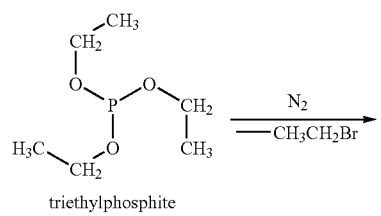
triethylphosphite

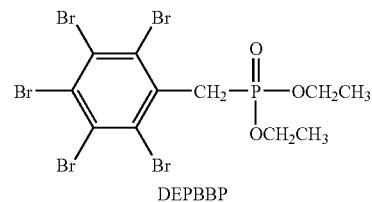
DEPBBP

Into a 500 ml round bottomed flask equipped with mechanical stirrer, nitrogen inlet, and a pipe to a cooled (under ice) trap, were placed pentabromobenzyl bromide (PBB-Br, FR-706, ICL-IP, 330 gr., 0.58 mol) and triethylphosphite (110 ml, (105 gr.) 0.63 mol).

The mixture was gradually heated. The temperature was raised from 25° C. up to 100° C. over 50 min. During this period of time, PBB-Br completely dissolved in the hot triethylphosphite and the solution became yellowish. Ethylbromide started to evolve at 95° C. The temperature of the heating oil was kept at 100° C. An exothermic behavior is observed. The temperature rose spontaneously in the reaction vessel to 105° C. The temperature then increased to 110° C. and the reflux became stronger till 136° C. The temperature then dropped to 117° C. At this point the temperature of the heating plate was raised to 150° C. The temperature was maintained at 150° C. for one hour. At 150° C. a vacuum pump was applied in order to distill the residue of ethylbromide and the slight excess of triethylphosphite. The distillate (52 gr. of ethylbromide) was trapped in the cold trap. The reaction mixture obtained consists of diethyl pentabromobenzylphosphonate (FR-564) in a molten state. The molten diethyl pentabromobenzylphosphonate may be directly used as a starting material for the process of the invention, as illustrated in Example 1.

The invention claimed is:

1. A compound having the formula:

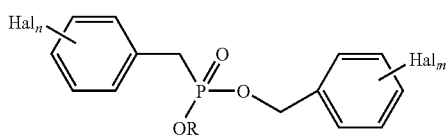

Wherein Hal independently indicates a halogen atom;
R is selected from the group consisting of a straight or branched, optionally substituted C1-C5 alkyl and halogenated benzyl; and
m and n are, independently, integers in the range between 3 and 5, inclusive.

2. A compound according to claim 1, wherein R is a straight or branched, optionally substituted C1-C5 alkyl group.

3. A compound according to claim 2, wherein n and m each equals 5.

4. A compound according to claim 3, wherein the ten halogen atoms attached to the aromatic rings are bromine atoms.

5. A compound according to claim 1, wherein R is halogenated benzyl.

6. A compound according to claim 5, wherein each of the three aromatic rings is perhalogenated.

7. A compound according to claim 6, wherein each of the three aromatic rings is perbrominated.

8. A compound according to claim 1, selected from the group consisting of:

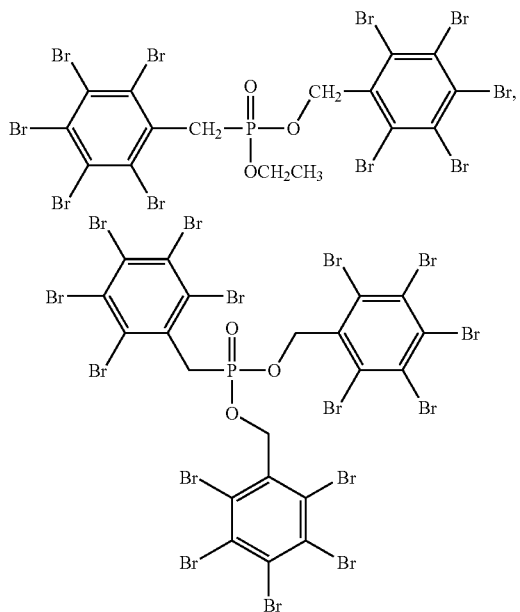

and their mixture.

9. A process for preparing a compound of formula (I) according to claim 1, which comprises reacting a compound of formula (II) and a compound of formula (III)

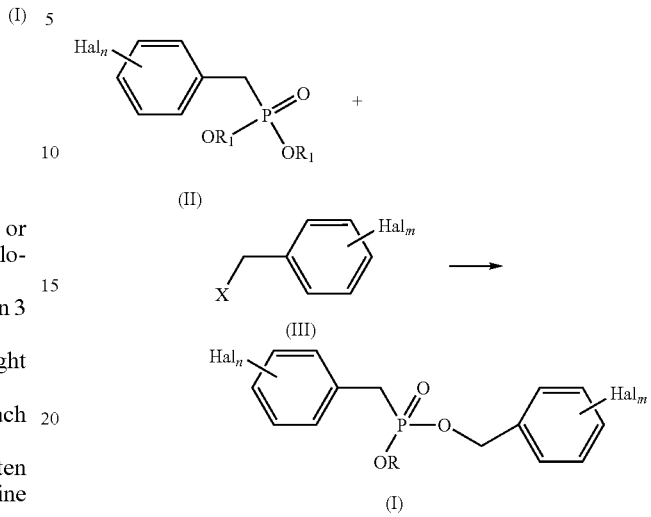

Wherein Hal, n, m and R have the meanings indicated above, $R_1$ is a straight or branched, optionally substituted C1-C5 alkyl group and X is a leaving group.

10. A process according to claim 9, which comprises providing the compound of Formula (II) in a liquid form, mixing said liquid with a compound of formula (III) at a temperature above the melting point of said compound of Formula (II) to form the product of Formula (I), and separating said product from the reaction mixture.

11. A process according to claim 10, wherein the compound of formula (II) is provided in-situ in a molten form, by means of reacting halogenated benzyl halide of formula (III) with trialkyl phosphite of the formula $(R_1O)_3P$, wherein said compound of formula (II) functions as an indigenous reaction liquid medium.

12. A process according to claim 11, which is one-pot process, which comprises reacting halogenated benzyl halide of formula (III) with trialkyl phosphite of the formula $(R_1O)_3P$ under heating, to obtain a compound of formula (II) in a liquid form, maintaining the reaction mixture at a temperature above the melting point of said compound (II) for a sufficient time to form the product of formula (I), and separating said product from the reaction mixture.

13. A formulation which comprises a flammable material and one or more compounds of formula (I) as defined in claim 1.

14. A formulation according to claim 13, wherein the flammable material is styrene-containing polymer.

* * * * *